(12) United States Patent
Salton

(10) Patent No.: US 8,947,661 B2
(45) Date of Patent: Feb. 3, 2015

(54) HIGH NUMERICAL APERTURE LIGHT SCATTERING INSTRUMENT FOR DETECTING PARTICLES IN FLUID

(75) Inventor: Scott H. Salton, Fremont, CA (US)

(73) Assignee: Lighthouse Worldwide Solutions, Inc., Fremont, CA (US)

( * ) Notice: Subject to any disclaimer, the term of this patent is extended or adjusted under 35 U.S.C. 154(b) by 1946 days.

(21) Appl. No.: 11/995,671

(22) PCT Filed: Jul. 12, 2006

(86) PCT No.: PCT/US2006/027174
§ 371 (c)(1),
(2), (4) Date: Aug. 24, 2011

(87) PCT Pub. No.: WO2007/009029
PCT Pub. Date: Jan. 18, 2007

(65) Prior Publication Data
US 2012/0140221 A1 Jun. 7, 2012

Related U.S. Application Data

(60) Provisional application No. 60/595,539, filed on Jul. 12, 2005.

(51) Int. Cl.
*G01N 21/00* (2006.01)
*G01N 21/53* (2006.01)
*G01N 15/02* (2006.01)
*G01N 15/14* (2006.01)
*G02B 19/00* (2006.01)

(52) U.S. Cl.
CPC ............ *G01N 21/53* (2013.01); *G01N 15/0205* (2013.01); *G01N 15/1456* (2013.01); *G02B 19/0014* (2013.01); *G02B 19/0076* (2013.01)
USPC .......................................... 356/337; 356/338

(58) Field of Classification Search
CPC .............. G01N 21/53; G01N 15/0205; G01N 15/1456; G01N 15/1459; G01N 2015/0222; G01N 2015/0244; G01N 2015/1447; G01N 2021/4707; G01N 21/94; G02B 19/0014; G02B 19/0076
USPC .................................................. 356/337–343
See application file for complete search history.

(56) References Cited

U.S. PATENT DOCUMENTS 4,830,494 A * 5/1989 Ishikawa et al. ............... 356/336

FOREIGN PATENT DOCUMENTS

JP 07035763 A * 2/1995 ............. G01P 13/00

* cited by examiner

*Primary Examiner* — Tri T Ton
(74) *Attorney, Agent, or Firm* — Michael L. Greenberg, Esq.; Greenberg & Lieberman, LLC

(57) ABSTRACT

A device (FIG. 2) that uses light to detect particles in fluid is disclosed. The device incorporates a lens and reflector on a flow cell to increase the numerical aperture of a subsequent light collection system without any increase in spherical aberration.

3 Claims, 2 Drawing Sheets

HIGH NUMERICAL APERTURE LIGHT SCATTERING INSTRUMENT FOR DETECTING PARTICLES IN FLUID

CROSS-REFERENCE TO RELATED APPLICATIONS

This application is a 371 of PCT/US06/27174, filed Jul. 12, 2006; which claims the benefit of U.S. provisional application Ser. No. 60/595,539 filed Jul. 12, 2005.

FIELD OF THE INVENTION

The present invention relates to particle sensors, and more particularly, to a particle sensor for fluid.

BACKGROUND OF THE INVENTION

A general understanding of the principles of the context of the present invention can be found in "Theoretical analysis of numerical aperture increasing lens microscope", S. B. Ippolito, B. B. Goldger, and M. S. Unlu, Journal of Applied Physics 97, 053105 (2005).

Conventional right angle (90 degree scatter) particle counters employ a planar flow cell and separate collection optics system to detect particles in fluid. The planar flow cell is required so that the surfaces can be highly polished and AR coated to minimize stray light and improve sensitivity. However, this optical configuration results in a limited numerical aperture that can lead to a classical reversal in the response curve as the amount of light actually decreases as particle sizes increase in the Mie regime making the device of little use in this regime. There is a need for an invention that effectively eliminates this problem.

In addition, there is a need for an invention that permits the numerical aperture of the collection system to be increased without introducing spherical aberration thereby allowing the device to detect smaller particles U.S. Pat. No. 4,728,190 refers to the use of lens in contact with a capillary or flow cell. However, these elements are part of a near forward geometry light scattering instrument (scattered light and light source centered on the same axis). Unlike the present invention, U.S. Pat. No. 4,728,190 applies to a right angle geometry light scattering instrument (scattered light and light source orthogonal to each other).

In addition, unlike the present invention, the primary purpose of the lens/capillary combination in U.S. Pat. No. 4,728,190 is to reduce stray light at the air/glass interface of the face of the capillary or flow cell in the path of the light source. This is not a benefit of the lens/reflector/flow cell combination in the present invention.

SUMMARY

The present invention provides an improved method for detecting particles in fluid. The present invention results in a single collection optic system with a high numerical aperture that provides improved response linearity through the Rayleigh and Mie Scatter size regimes and increased particle sensitivity over conventional instruments.

DETAILED DESCRIPTION

Figure 1:
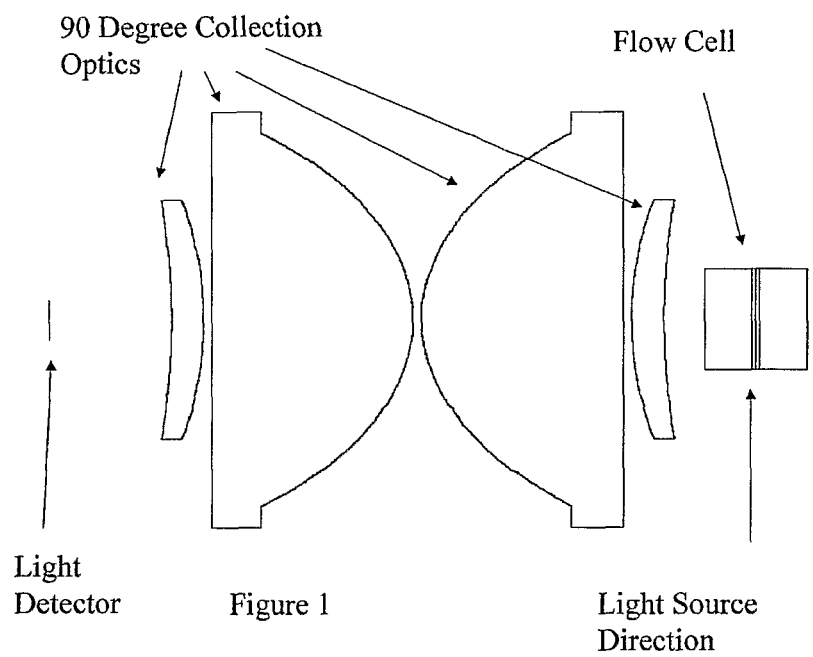
FIG. 1 shows an example of relevant art to the present invention.

A classical 90 degree light scatter collection optics system is shown in FIG. 1. It is comprised of a planar flow cell and a series of lenses for collecting scattered light. The direction of the particle flow, light source and collection optics are all orthogonal and 90 degrees from one another.

Figure 2:
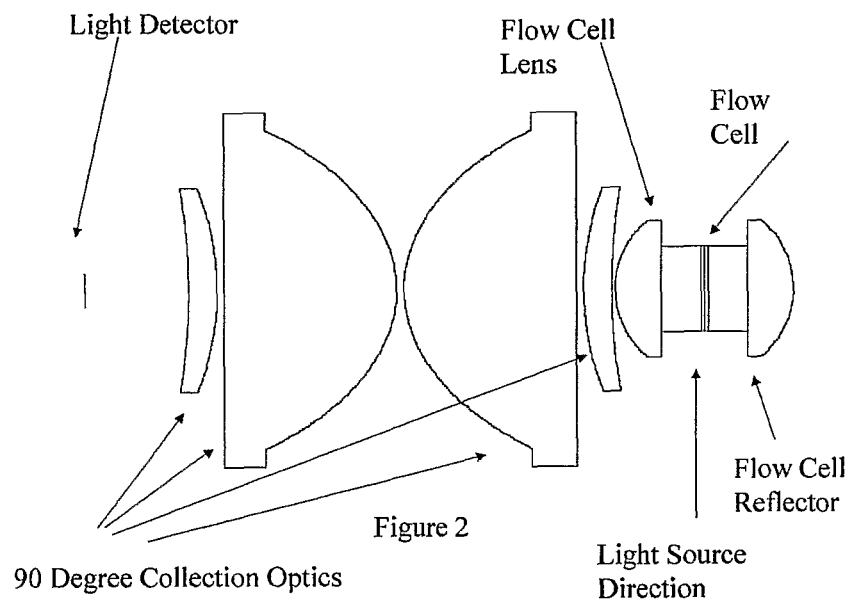
FIG. 2 shows the present invention.

In FIG. 2, an optional lens and reflector on the flow cell improve the light collection capabilities of the instrument as described previously. Again, the direction of the particle flow, light source and collection optics are all orthogonal and 90 degrees from one another.

The Flow Cell Reflector serves to reflect the light scattered in its direction within the glass medium back to the center of the flow cell making the light available for the collection system. By keeping this light collection path entirely in the glass medium the numerical aperture is increased for the reflector. The Flow Cell Lens serves to increase the light gathering capability of the 90 Degree Collection Optics without aberration.

The present invention is designed to function as follows. First, the light source will illuminate the fluid as it travels through the flow cell. Such illumination will scatter off of any particles contained in the fluid. The flow cell lenses (when in use), will focus this light into the center of the flow cell. From the flow cell lenses, the scattered light will be emitted into a series of 90 degree collection optics. When flow cell lenses are not employed, the light will be naturally scattered into the 90 degree collection optics. Light that is emitted into the 90 degree collection optics from the flow cell lenses will be more intense then light that is simply captured by the 90 degree collection optics without the benefit of the flow cell lenses. Finally, after passing through the 90 degree collection optics, the light will be focused by the 90 degree collection optics upon the light detection sensor. When the sensor detects light, the system will conclude that there is a particle present in the flow cell. The resulting light intensity received by the light detector will be proportional to the particle size.

I claim:

1. A device for optically detecting particles in fluid comprising:
a light collection system which maximizes the light intensity output scattered from a particle in fluid resulting in a monotonic relationship between scattered light intensity and particle size for spherical polystyrene particles with light sources having wavelengths in the range of 430 nm to 1500 nm suspended in fluids with optical indexes ranging between 1.3 and 1.5, said light collection system comprising:
a light source;
a flow cell;
a reflector on said flow cell;
a lens on said flow cell; and
wherein glass is used as a medium for which light to travel.

2. The device of claim 1, wherein said flow cell is positioned between said reflector and said lens.

3. The device of claim 2, further comprising 90 degree collection optics positioned between said flow cell lens and a light detector.

* * * * *